United States Patent
Appleby et al.

(10) Patent No.: US 8,679,569 B2
(45) Date of Patent: Mar. 25, 2014

(54) SUCROSE POLYESTERS

(75) Inventors: Donald Benjamin Appleby, Cincinnati, OH (US); Deborah Jean Back, Cleves, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 190 days.

(21) Appl. No.: 12/957,759

(22) Filed: Dec. 1, 2010

(65) Prior Publication Data

US 2011/0129592 A1 Jun. 2, 2011

Related U.S. Application Data

(60) Provisional application No. 61/265,373, filed on Dec. 1, 2009.

(51) Int. Cl.
*A23D 9/007* (2006.01)

(52) U.S. Cl.
USPC ............ 426/611; 426/612; 536/115; 536/119

(58) Field of Classification Search
USPC .................................................. 426/611, 612
See application file for complete search history.

(56) References Cited

U.S. PATENT DOCUMENTS

| | | | |
|---|---|---|---|
| 4,810,516 A | 3/1989 | Kong-Chan | |
| 4,952,687 A | 8/1990 | Bodor et al. | |
| 5,071,669 A | 12/1991 | Seiden | |
| 5,194,281 A | 3/1993 | Johnston et al. | |
| 5,504,202 A | 4/1996 | Hutchison | |
| 5,518,754 A | 5/1996 | Miller et al. | |

FOREIGN PATENT DOCUMENTS

| | | |
|---|---|---|
| EP | 0378876 | * 12/1989 |
| EP | 0 424 067 A2 | 4/1991 |
| WO | WO 94/09638 | 5/1994 |
| WO | WO 00/44760 | 8/2000 |

OTHER PUBLICATIONS

Swern, D. 1979. Bailey's Industrial OIl and Fat Products, vol. 1, 4$^{th}$ edition. John Wiley & Sons, New York. p. 416, 417, 432. 431, 432.*
International Search Report mailed Mar. 31, 2011, 3 pages.

* cited by examiner

*Primary Examiner* — Carolyn Paden
(74) *Attorney, Agent, or Firm* — Melody A. Jones

(57) ABSTRACT

Disclosed herein are compositions that include a blend of sucrose polyesters, wherein each sucrose polyester includes a sucrose moiety and a plurality of fatty acid ester moieties, wherein a percentage range of the combined fatty acid ester moieties of the sucrose polyesters in the blend have a carbon chain that has trans content.

18 Claims, No Drawings

SUCROSE POLYESTERS

CROSS REFERENCE TO RELATED APPLICATION

This application claims priority to U.S. Provisional Application Ser. No. 61/265,373, filed Dec. 1, 2009.

FIELD OF THE INVENTION

The instant invention relates to sucrose polyester compositions, products comprising such compositions, as well as methods of making and using such compositions and products.

BACKGROUND OF THE INVENTION

Sucrose polyesters, because of their bulk and shape, form different crystalline structures having melting profiles that are quite dissimilar to certain natural fats and oils. Typically, sucrose polyesters meeting the compositional restrictions of Olestra®, as approved by the United States Food and Drug Administration, have a very flat melting profile across a broad temperature range.

By hydrogenating sucrose polyesters, it is possible to increase the melting point by converting sucrose polyesters containing unsaturated carbon chains into sucrose polyesters containing saturated carbon chains; however, the melting profile of such sucrose polyesters remains flat, resulting in a high solids content at body temperatures (approximately 37° C.). When these sucrose polyesters are incorporated into food products, such a high solids content causes an undesirable, waxy mouth feel for the consumer eating the food product. This is particularly disadvantageous when the sucrose polyesters are incorporated into chocolate or other confections because such products are favored by the consumer, in part, due to a particular mouth feel associated with these types of products. In other words, certain food products (e.g., chocolates, frostings, icings, etc.) may be particularly preferred because of the products' ability to melt in a consumer's mouth. Thus, there remains a continuing need for a fat substitute that can be incorporated into food products, wherein the fat substitute provides a consumer with a desired mouth-feel when eating the food products.

SUMMARY OF THE INVENTION

Sucrose polyester compositions, products comprising such compositions, as well as methods of making and using such compositions and products, are disclosed.

In one embodiment, the present disclosure provides for a composition comprising a blend of sucrose polyesters, wherein each sucrose polyester comprises a sucrose moiety and a plurality of fatty acid ester moieties, wherein from about 90% to about 100% of the sucrose polyesters in the blend are selected from a group consisting of octa-, hepta-, and hexa-sucrose polyesters, from about 25% to about 50% of the combined fatty acid ester moieties of the sucrose polyesters in the blend comprise a carbon chain that contains trans content, and from about 60% to about 100% of the combined fatty acid ester moieties of the sucrose polyesters in the blend comprise a $C_{18}$ carbon chain, with the balance of the fatty acid ester moieties of the sucrose polyesters in the blend comprising a carbon chain independently selected from $C_{12}$-$C_{17}$ or $C_{19}$-$C_{22}$ carbon chains.

In another embodiment, the present disclosure provides for a process of making the above detailed sucrose polyesters that includes the step of transesterifying a sucrose molecule with an ester, the ester being produced via esterifying a hydrogenated oil that comprises a trans fatty acid content of from about 25% to about 50% with a lower alcohol.

In another embodiment, the present disclosure provides for a food product that includes a sucrose polyester and at least one food ingredient.

In yet another embodiment, the present disclosure provides for a method of providing a reduced fat content food product having an improved mouth feel comprising the step of incorporating sucrose polyester into a food product.

DETAILED DESCRIPTION OF THE INVENTION

As used herein, the articles "a" and "an" when used in a claim, are understood to mean one or more of what is claimed or described.

As used herein, the terms "include", "includes" and "including" are meant to be non-limiting.

As used herein, the term "comprising" means various components conjointly employed in the preparation of the compositions of the present disclosure. Accordingly, the terms "consisting essentially of" and "consisting of" are embodied in the term "comprising".

As used herein, the "complete melting point" means the temperature at which the last visible traces of solids disappear. The complete melting point of a given composition or component is measured in accordance with AOCS Method Cc 1-25 (American Oil Chemists' Society).

As used herein, the term "lower alcohol" means a $C_1$, $C_2$, $C_3$, or $C_4$ alcohol, and combinations thereof.

As used herein, the term "melting point" means the temperature at which a component starts to change from the solid to the liquid phase.

As used herein, the term "octa-sucrose polyester," means that eight of the available hydroxyl moieties on a sucrose molecule are esterified with a fatty acid; the term "hepta-sucrose polyester" means that seven of the available hydroxyl moieties on a sucrose molecule are esterified with a fatty acid; the term "hexa-sucrose polyester" means that six of the available hydroxyl moieties on a sucrose molecule are esterified with a fatty acid; the term "penta-sucrose polyester" means that five of the available hydroxyl moieties on a sucrose molecule are esterified with a fatty acid.

As used herein, "Solid Fat Content" or "SFC" means the percentage of a fat or oil that exists in crystalline form at a given temperature.

As used herein, the Solid Fat Index, or "SFI" is an empirical measure of solid fat content (SFC) at standardized temperature check points.

As used herein, the term "sucrose polyester" means compositions comprising sucrose and fatty acids with at least five of the available hydroxyl moieties on a sucrose molecule esterified with a fatty acid.

As used herein, all tests and measurements, unless otherwise specified, are made at 25° C.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

To be useful in chocolates and other confections (e.g., coatings, frosting, fillings, icings, baked goods, candy and other food products), non-caloric fat substitutes are ideally solid at room temperature but have a melting point near or at body temperature. The melting point and melting profile of the non-caloric fat substitutes utilized in chocolates and other confections contribute to the desired mouth-feel associated with these types of food products. Ideally, the non-caloric fat substitutes will contain little to no solids at body temperature (about 37° C.). As stated above, a problem in the art as it relates to employing particular embodiments of sucrose polyesters in these types of food products is the ability to provide a food product that delivers to the consumer a desired mouth feel.

Applicants have further recognized that the process by which sucrose polyesters are made may influence the melting profile. Specifically, Applicants have recognized that sucrose polyesters made by using fats/oils that have been hydrogenated before formation of the sucrose polyester do not have the same solid fat index as sucrose polyesters that are hydrogenated after formation of the sucrose polyester.

Disclosed herein are sucrose polyesters having a melting profile such that the sucrose polyesters provide consumers a desired mouth feel suited for chocolate, confections, or other like food products. Processes of making such sucrose polyesters, and food compositions comprising such sucrose polyesters, are also disclosed.

Sucrose Polyester:

Disclosed herein are compositions comprising a blend of sucrose polyesters, wherein each sucrose polyester comprises a sucrose moiety and a plurality of fatty acid ester moieties, wherein:
  a. from about 90% to about 100%, or from about 95% to about 100%, by weight, of the sucrose polyesters in the blend are selected from a group consisting of octa-, hepta-, and hexa-sucrose polyesters;
  b. from about 25% to about 50%, or from about 40% to about 50%, or from about 40% to about 45%, by weight, of the combined fatty acid ester moieties of the sucrose polyesters in the blend comprise a carbon chain that contains trans content; and
  c. from about 60% to about 100%, or from about 75% to about 95%, or from about 85% to about 90%, by weight, of the combined fatty acid ester moieties of the sucrose polyesters in the blend comprise a $C_{18}$ carbon chain, with the balance of the fatty acid ester moieties of the sucrose polyesters in the blend comprising a carbon chain independently selected from $C_{12}$-$C_{17}$ or $C_{19}$-$C_{22}$ carbon chains.

In one aspect, from about 40% to about 90%, or from about 50% to about 85%, or from about 60% to about 70%, or about 75%, by weight, of the combined fatty acid ester moieties of the sucrose polyesters in the blend may comprise an unsaturated carbon chain.

In one aspect, the carbon chains that contain a trans content may be $C_{18}$ carbon chains selected from a group consisting of $C_{18:1}$ trans, $C_{18:2}$ trans, and combinations thereof.

In one aspect, the composition may comprise a fatty acid ester derived from an edible oil comprising at least one trans fatty acid. In one aspect, the edible oil comprising a trans fatty acid may be selected from rapeseed oil, tallow oil, coconut oil, babassu oil, corn oil, lard, olive oil, peanut oil, sesame oil, soybean oil, canola oil, palm oil, sunflower oil, safflower oil, cottonseed oil, and combinations thereof.

In one aspect, the composition may exhibit a thixotropic area of from about 50,000 to about 300,000, or from about 100,000 to about 200,000 pascals/second at 33.3° C., as measured using the Test Methods described herein. In one aspect, the composition may exhibit a thixotropic area of from about 50,000 to about 100,000 pascals/second at 33.3° C., as measured using the Test Methods described herein.

In one aspect, the composition may comprise:
  a) from about 60% to about 99%, based on total weight of the sucrose polyester blend, of a sucrose polyester having a complete melting point of less than about 40° C., wherein the sucrose polyester may be liquid at room temperature; and
  b) from about 1% to about 40%, or from about 2% to about 20%, or from about 5% to about 8%, based on total weight of the sucrose polyester blend, of a sucrose polyester having a complete melting point of from about 40° C. to about 100° C., or from about 60° C. to about 75° C., wherein the sucrose polyester may be solid at room temperature.

In one aspect, the composition may comprise, based on total weight of the sucrose polyester blend, from about 0% to about 0.5% penta-sucrose polyesters.

In one aspect, the composition may have a Solid Fat Index such that the composition comprises, based on total weight of the sucrose polyester blend:
  a) from about 45% to about 75%, or from about 65% to about 75%, solids at 10° C.;
  b) from about 5% to about 25%, or from about 15% to about 20%, solids at 30° C.; and
  c) from about 5% to about 10%, or from about 7% to about 10%, solids at 40° C.

In one aspect, a process of making a composition as described herein is disclosed. In one aspect, the process may comprise a step of transesterifying a sucrose molecule with an ester, the ester being produced via esterification of a hydrogenated oil comprising a trans fatty acid content of from about 25% to about 50%, with a lower alcohol.

In one aspect, the process may comprise the step of transesterifying a sucrose molecule with a hydrogenated oil comprising a trans fatty acid content of from about 25% to about 50%.

In one aspect, the process may comprise the steps of:
  a.) partially hydrogenating an oil or methyl ester derived from an oil to produce an oil or methyl ester that comprises carbon chains having a trans fatty acid content of from about 25% to about 50%; and
  b.) transesterifying a sucrose molecule with said oil or methyl ester that comprises carbon chains having a trans fatty acid content of from about 25% to about 50% to produce an esterified sucrose molecule that comprises carbon chains having a trans fatty acid content of from about 25% to about 50%.

Sucrose polyester blends that include sucrose polyesters that are produced by the processes detailed above may have a preferred mouth feel when eaten by consumers when compared to post hydrogenated sucrose polyesters.

In one aspect, the oil may comprise an edible oil. In one aspect, the oil may comprise an oil selected from rapeseed oil, tallow oil, coconut oil, babassu oil, corn oil, lard, olive oil, peanut oil, sesame oil, soybean oil, canola oil, palm oil, sunflower oil, safflower oil, cottonseed oil, and combinations thereof.

In one aspect, a food composition comprising a sucrose polyester as described herein and at least one food ingredient is disclosed. In this aspect, the food composition may comprise a sucrose polyester, wherein the food composition may comprise, based on total weight of the food composition, from about 1% to 99%, or from about 10% to about 90%, or from about 20% to about 80% of a sucrose polyester composition as described herein. In one aspect, the food ingredient may be selected from cocoa powder, cocoa butter, chocolate liquor, sugar, non-calorie sweetener, partially or wholly non-digestible carbohydrate bulking agent, triglycerides, emulsifiers, water, egg products, sugar, flour, non-pre-gelatinized starch, egg solids, protein solids, flavorings, and mixtures thereof. Exemplary food compositions may include chocolate, chocolate coatings, baked goods, frostings, candy products, and the like. In another aspect, sucrose polyesters as described herein may be employed to deep fry or surface fry food compositions.

In one aspect, a method of providing a reduced fat content food product having an improved mouth feel is disclosed, wherein the method may comprise the step of incorporating a composition as described above into a food composition. In one aspect, the food composition is chocolate.

TEST METHODS

For purposes of the present application, Solid Fat Content; Trans Content; Thixotropic Area and Fatty Acid Composition are determined as follows:

Solid Fat Content ("SFC")—A sample of the test composition is heated to a temperature of 140° F. (60° C.) for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; and at 32° F. (0° C.) for 15 minutes. After tempering, the SFC values of the sample at temperatures of 50° F. (10° C.), 70° F. (21.1° C.), 80° F. (26.7° C.), 92° F. (33.3° C.) and 98.6° F. (37° C.), is determined by pulsed nuclear magnetic resonance (PNMR) after equilibration for 30 minutes at each temperature. The method for determining SFC values by PNMR is described in Madison and Hill, J. Amer. Oil Chem. Soc., Vol. 55 (1978), pp. 328-31. Measurement of SFC by PNMR is also described in A.O.C.S. Official Method Cd. 16-81, Official Methods and Recommended Practices of The American Oil Chemists Society. 3rd. Ed., 1987.

Measurement of Trans Content—The trans content, or trans fatty acid content, as a percentage of the double bonds of the unsaturated fatty acids in the polyester sample, is determined by Fourier transform infrared spectrophotometry (FTIR). The FTIR method used is described in AOCS Official Method Cd 14d-99, Reapproved in 2009, "Rapid Determination of Isolated trans Geometric Isomers in Fats and Oils by Attenuated Total Reflection Infrared Spectroscopy" and is accurate for samples containing equal to or greater than 1% trans isomer. The trans value obtained by FTIR, together with the fatty acid composition of the polyester sample, is used to calculate the ratio of cis:trans double bonds.

Determination of Thixotropic Area—Samples are prepared by transferring about 8.0 grams of sample into a 57 mm aluminum pan. The sample is heated to above 113° C. until completely liquid, then tempered by cooling to 29° C. with agitation. The sample is then held at 21° C. for 7 days. Using a suitable cone and plate rheometer (such as Contraves Rheomat 115A, cone CP-6) maintained at 37.8° C. and capable of measuring the non-Newtonian flow curve hysteresis for ascending and descending shear rates programmed from 0 to 800 s-1, the rheometer is held at 0 s-1 for 120 seconds, then raised to 800 sec-1 in 7.5 minutes, held for 1 s, then decreased to 0 s-1 in 7.5 min to measure the thixotropic area. The rheometer accuracy is checked with viscosity standards such as Cannon ASTM Certified Viscosity Standards, S-2000 and N-350 or equivalent. A sufficient amount of the test sample is placed on the rheometer plate to fill the gap between the plate and cone. The thixotropic area is then measured.

Determination of Fatty Acid Composition—The fatty acid composition of the sucrose polyesters disclosed may be measured by gas chromatography. First, fatty acid methyl esters of the sucrose polyesters are prepared via any standard method known in the art (for example, via transesterification using sodium methoxide), and then separated on a capillary column (Supelco SP2340, 60×0.32 mm×0.2 micron), utilizing a Hewlett-Packard Model 6890 gas chromatograph equipped with a Flame Ionization Detector and a Hewlett-Packard automatic sampler, Model 7683. The fatty acid methyl esters are separated by chain length, degree of unsaturation and isomeric variations including cis, trans and conjugation. The method is programmed to run for 50 minutes ramping the temperature from 140-195° C. with and injection temperature of 250° C. and a detection temperature of 325° C. For calibration, the fatty acid methyl ester reference standard Nuchek Prep (#446) is used.

EXAMPLES

Example 1

20 kilograms of partially hydrogenated soybean oil (Product No. LP426 available from Golden Brands of Louisville, Ky.) are placed in a 30 liter reaction vessel equipped with a stirrer and reflux condenser and reacted with 5375 grams of methanol using 226.6 grams of sodium methoxide as catalyst. The mixture is stirred at 65° C. for 6 hours; methanol is allowed to reflux. The reaction mixture is then allowed to rest without stirring until the glycerin byproduct settles to the bottom of the vessel. The glycerin layer is then removed and the methyl ester layer is washed with 10% water by weight of the methyl ester at 30° C. to remove residual methanol, catalyst, soap and any remaining glycerin. The wash process is repeated two additional times. The methyl esters are then dried under vacuum (25 mm Hg) at 95° C. The methyl esters are then distilled in a wiped film evaporator at 195° C. and ~1 mm Hg absolute pressure to separate the methyl esters from any un-reacted glycerides. The methyl esters have the following fatty acid composition:

| | |
|---|---|
| $C_{16}$ | 12% |
| $C_{18}$ | 10.9% |

| | |
|---|---|
| $C_{18:1}$ trans | 36.4% |
| $C_{18:1}$ cis | 29.3% |
| $C_{18:2}$ trans | 1.6% |
| $C_{18:2}$ cis | 0.3% |
| $C_{18:3}$ cis | 0% |

Example 2

A liquid sucrose polyester sample is prepared using the methyl ester prepared in Example 1. 1073 grams of the methyl ester of Example 1, 212 grams of a milled mixture of sucrose and potassium palmitate and 4.5 grams of potassium carbonate are added to a 5 liter reaction vessel equipped with overhead mechanical stirrer, heating mantel and nitrogen sparge tube. The contents of the reaction flask are heated to 135° C. with vigorous stirring and nitrogen sparge for ~3 hours. Another 1073 grams of the methyl ester of Example 1 is then added along with 4.5 grams of $K_2CO_3$. The reaction is continued at 135° C. until the total conversion of sucrose polyester measures >75% octa-ester.

The crude reaction mix from above is then hydrated with ~230 mls water and the contents of the flask are allowed to set without stirring. The top layer (oil layer) is decanted away from the hydrated soap layer. The oil layer is then dried at 95° C. (25 mm Hg) until free of residual water. The oil layer is then bleached with 1% Trisyl (available from W.R. Grace) and pressure filtered to remove the bleaching earth. The treated oil layer is then passed through a wiped film evaporator to remove residual methyl esters. The resulting liquid sucrose polyester has the following properties:

| Sucrose ester distribution | |
|---|---|
| Sucrose octa-ester | 81.6% |
| Sucrose hepta-ester | 18.1% |
| Sucrose hexa-ester | 0.3% |
| Sucrose penta-ester | 0.0% |
| Fatty Acid Composition | |
| $C_{16}$ | 12.6% |
| $C_{18}$ | 10.6% |
| $C_{18:1}$ trans | 36.9% |
| $C_{18:1}$ cis | 31.8% |
| $C_{18:2}$ trans | 1.4% |
| $C_{18:2}$ cis | 0.6% |
| $C_{18:3}$ cis | 0.3% |

Example 3

93 grams of the liquid sucrose polyester from Example 2 are combined with 7 grams of a solid sucrose polyester having a melting point of 65° C. to give a sucrose polyester blend. The solid sucrose polyester has the following properties:

| Sucrose ester distribution of the solid Component | |
|---|---|
| Sucrose octa-ester | 78.9% |
| Sucrose hepta-ester | 21.0% |
| Sucrose hexa-ester | 0.2% |
| Sucrose penta-ester | 0.0% |
| Fatty Acid Composition of the Solid Component | |
| $C_{16}$ | 1.5% |
| $C_{18}$ | 3.9% |
| $C_{18:1}$ cis | 8.3% |
| $C_{18:2}$ cis | 3.0% |
| $C_{20:0}$ | 6.8% |
| $C_{22:0}$ | 76% |

The resulting sucrose polyester blend (comprising the liquid sucrose polyester from Example 2 and the above detailed solid sucrose polyester) has the following properties:

| Sucrose ester distribution | |
|---|---|
| Sucrose octa-ester | 80.6% |
| Sucrose hepta-ester | 19.1% |
| Sucrose hexa-ester | 0.3% |
| Sucrose penta-ester | 0.0% |
| Fatty Acid Composition | |
| $C_{16}$ | 12.4% |
| $C_{18}$ | 10.5% |
| $C_{18:1}$ trans | 35.1% |
| $C_{18:1}$ cis | 31.1% |
| $C_{18:2}$ trans | 3.3% |
| $C_{18:2}$ cis | 1.7% |
| $C_{18:3}$ cis | 0.6% |
| $C_{20}$ | 0% |
| $C_{22}$ | 5.3% |
| Thixotropic area: | 53,000 Pa/sec @ 33.3° C. |
| SFC | |
| 10° C. | 64.2% |
| 20° C. | 32.5% |
| 30° C. | 7.5% |
| 40° C. | 5.1% |

Example 4

The properties of the sucrose polyester blend of Example 3 were compared to those of a commercially available sucrose polyester blend marketed by The Procter & Gamble Company under the Olean® brand name. The particular Olean® product utilized in this example is produced from partially hydrogenated soybean oil, in which the hydrogenation conditions are chosen to minimize the formation of trans fatty acid isomers. The fatty acid composition and Solid Fat Contents of both samples are compared below:

| Fatty Acid Composition | Sample Blend from Example 3 | Olean ® brand olestra |
|---|---|---|
| $C_{16}$ | 12.4% | 12.7% |
| $C_{18}$ | 10.5% | 6.7% |
| $C_{18:1}$ trans | 35.1% | 13.5% |
| $C_{18:1}$ cis | 31.1% | 40.3% |
| $C_{18:2}$ trans | 3.3% | 3.0% |
| $C_{18:2}$ cis | 1.7% | 17.4% |
| $C_{18:3}$ cis | 0.6% | 0.5% |
| $C_{20}$ | 0% | 0.7% |
| $C_{22}$ | 5.3% | 3.5% |
| SFC | | |
| 10° C. | 64.2% | 10.8% |
| 20° C. | 32.5% | 7.6% |
| 30° C. | 7.5% | 6.1% |
| 40° C. | 5.1% | 5.6% |
| Sucrose ester distribution | | |
| Sucrose octa-ester | 80.6% | 80.5% |
| Sucrose hepta-ester | 19.1% | 19.2% |
| Sucrose hexa-ester | 0.3% | 0.3% |
| Sucrose penta-ester | 0% | 0% |

-continued

| Fatty Acid Composition | Sample Blend from Example 3 | Olean ® brand olestra |
|---|---|---|
| Thixotropic area | 53,000 Pa/sec @ 33.3° C. | 52,000 Pa/sec @ 33.3° C. |

Example 5

Sucrose polyesters produced on a commercial scale from soybean oil are hydrogenated to produce a liquid sucrose polyester fraction with a similar level of unsaturated fatty acids as the product described in Example 2. When 94 grams of this liquid fraction is blended with 6 grams of the same solid sucrose polyester fraction described and utilized in the sample blend of Example 3, the result is a blend comprising post hydrogenated sucrose polyesters. The properties of this blend were compared with the properties of the sucrose polyester blend of Example 3.

| Fatty Acid Composition | Sample Blend from Example 3 | Blend w/Post Hydrogenated Sucrose Polyesters |
|---|---|---|
| $C_{16}$ | 12.4% | 12.7% |
| $C_{18}$ | 10.5% | 6.7% |
| $C_{18:1}$ trans | 35.1% | 13.5% |
| $C_{18:1}$ cis | 31.1% | 40.3% |
| $C_{18:2}$ trans | 3.3% | 3.0% |
| $C_{18:2}$ cis | 1.7% | 17.4% |
| $C_{18:3}$ cis | 0.6% | 0.5% |
| $C_{20}$ | 0% | 0.7% |
| $C_{22}$ | 5.3% | 3.5% |
| SFC | | |
| 10° C. | 64.2% | 52.1% |
| 20° C. | 32.5% | 29.0% |
| 30° C. | 7.5% | 21.8% |
| 40° C. | 5.1% | 13.3% |
| Sucrose ester distribution | | |
| Sucrose octa-ester | 80.6% | 78.5% |
| Sucrose hepta-ester | 19.1% | 21.2% |
| Sucrose hexa-ester | 0.3% | 0.3% |
| Sucrose penta-ester | 0% | 0% |

Example 6

62 g cocoa powder, 173 g whole milk solids, 0.6 g vanillin and 580 g sucrose are blended. 216 g of the sucrose polyester blend of Example 3 is added and the mixture is again blended. The blended mixture is then passed through a Lehman Four-roll Refiner twice (NIP pressure of 200 psi). Melted chocolate liquor (55 g) is then added to the refined mixture and then dry conched for 3 hours at 60° C. using a Hobart C-100 mixer set at speed #2. The temperature is then reduced to 50° C. and 50 g more Olean® (High Elaidic version) and 0.6 g lecithin is added. The mixture is then wet conched at 52° C. for 16 hrs at speed #1. Another 55 g of the sucrose polyester blend of Example 3 is added and the blend is cooled to 40° C., poured into molds and tempered as follows; 10° C. for 16-18 hrs, 15° C. for 24 hrs, 21° C. for 24 hrs.

Example 7

80 g of sucrose and 20 g of the sucrose polyester blend of Example 3 is mixed at 60° C. 3 g water is then added along with 0.3 g lecithin. The mixing is continued at 60° C. using a Hobart C-100 mixer until the water is removed. 26 g of non-fat dry milk solids are then added along with 12 g of cocoa powder, 3.5 g cocoa butter, and 2 g of the sucrose polyester blend of Example 3. The product is mixed for another 2-3 hours and then 15 g more of the sucrose polyester of Example 3 is added with 0.4 g lecithin. The mixing is continued without heating until the product has cooled to ~40° C. The mixture is then poured into molds and tempered as described in Example 6.

Example 8

90 g of a commercially available, 85% cacao extra dark chocolate bar is heated in a double boiler to a complete melt at 125° F. To the melted chocolate, 14.4 g of powdered confectionary sugar is added and mixed with a spatula. 28.6 g of the sucrose polyester blend of Example 3 is then added. The mixture is taken off the double boiler and another 10 g of the commercially available, 85% cacao extra dark chocolate bar is added to the mixture and melted into the mixture with stifling until the mixture cools to 115° F. This step of adding the additional 10 g of chocolate bar to the mixture is used to "seed" the lipid crystals to the desired polymorphic form. The chocolate mixture is then poured into bite size moulds and placed in the refrigerator to cool. The chocolate mixture hardens upon cooling and is removed from the moulds.

Example 9

90 g of the same commercially available, 85% cacao extra dark chocolate bar from Example 8 is heated in a double boiler to a complete melt at 125° F. To the melted chocolate, 14.4 g of powdered confectionary sugar is added and mixed with a spatula. 28.6 g of the commercially available Olean® detailed in Example 4 is then added. The mixture is taken off the double boiler and another 10 g of the commercially available, 85% cacao extra dark chocolate bar is added to the mixture and melted into the mixture with stirring until the product cools to 115° F. This step of adding the additional 10 g of chocolate bar to the mixture is used to "seed" the lipid crystals to the desired polymorphic form. The chocolate mixture is then poured into bite size moulds and placed in the refrigerator to cool. However, the chocolate mixture in this example did not sufficiently harden to be handled in a solid form.

Example 10

90 g of the same commercially available, 85% cacao extra dark chocolate bar from Examples 8 and 9 is heated in a double boiler to a complete melt at 125° F. To the melted chocolate, 14.4 g of powdered confectionary sugar is added and mixed with a spatula. 28.6 g of the post hydrogenated sucrose polyester blend from Example 5 is then added. The mixture is taken off the double boiler and another 10 g of the commercially available, 85% cacao extra dark chocolate bar is added to the mixture and melted into the mixture with stirring until the product cools to 115° F. This step of adding the additional 10 g of chocolate bar to the mixture is used to "seed" the lipid crystals to the desired polymorphic form. The chocolate mixture is then poured into bite size moulds and placed in the refrigerator to cool. The chocolate mixture hardens upon cooling and is removed from the moulds.

Results of Blind Testing for Mouth Feel:

A blind testing was conducted to evaluate mouth feel preference between the chocolate prepared in accordance with Example 8 and the chocolate prepared in accordance with Example 10. Seven test subjects blindly tasted a sample of the chocolate prepared in accordance with Example 8 and the chocolate prepared in accordance with Example 10 and then were asked which chocolate was preferred for mouth feel, also known as mouth-melting characteristics. All seven of the test subjects preferred the chocolate prepared in accordance with Example 8 over the chocolate prepared in accordance with Example 10 for mouth feel. The test subjects described the mouth feel characteristics of the chocolate prepared in accordance with Example 8 as cleaner and less waxy when compared with the chocolate prepared in accordance with example 10.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a blend of sucrose polyesters, wherein each sucrose polyester comprises a sucrose moiety and a plurality of fatty acid ester moieties, wherein:
   a. from about 90% to about 100% of the sucrose polyesters in the blend are selected from a group consisting of octa-, hepta-, and hexa-sucrose polyesters;
   b. from about 25% to about 50% of the combined fatty acid ester moieties of the sucrose polyesters in the blend comprise a carbon chain that contains trans content; and
   c. from about 60% to about 100% of the combined fatty acid ester moieties of the sucrose polyesters in the blend comprise a $C_{18}$ carbon chain, with the balance of the fatty acid ester moieties of the sucrose polyesters in the blend comprising a carbon chain independently selected from $C_{12}$-$C_{17}$ or $C_{19}$-$C_{22}$ carbon chains;
   and further wherein the sucrose polyester blend comprises, based on total weight of the sucrose polyester blend, a Solid Fat Index of:
   d. from about 45% to about 75% solids at 10° C.;
   e. from about 5% to about 25% solids at 30° C.; and
   f. from about 5% to about 10% solids at 40° C.

2. A composition according to claim 1, wherein about 40% to about 90% of the combined fatty acid ester moieties of the sucrose polyesters in the blend comprise an unsaturated carbon chain.

3. A composition according to claim 1, wherein the carbon chains that contain a trans content are $C_{18}$ carbon chains selected from a group consisting of $C_{18:1}$ trans, $C_{18:2}$ trans, and combinations thereof.

4. A composition according to claim 1, wherein the fatty acid ester moieties are derived from an edible oil comprising at least one trans fatty acid.

5. A composition according to claim 4, wherein the fatty acid ester moieties are derived from an oil selected from a group consisting of rapeseed oil, tallow oil, coconut oil, babassu oil, corn oil, lard, olive oil, peanut oil, sesame oil, soybean oil, canola oil, palm oil, sunflower oil, safflower oil, cottonseed oil, and combinations thereof.

6. A composition according to claim 1 comprising:
   a. from about 60% to about 99%, based on the total weight of the sucrose polyester blend, of sucrose polyesters having a complete melting point of less than about 40° C.; and
   b. from about 1% to about 40%, based on the total weight of the sucrose polyester blend, of sucrose polyesters having a complete melting point of from about 40° C. to about 100° C.;
   wherein the composition exhibits a thixotropic area of from about 50,000 to about 300,000 pascals/second at 33.3° C.

7. A composition according to claim 1 comprising, based on the total weight of the sucrose polyester blend, from about 0% to about 0.5% penta-sucrose polyesters.

8. A process of making the composition according to claim 1, comprising the step of transesterifying a sucrose molecule with an ester, said ester being produced via esterifying a hydrogenated oil that comprises a trans fatty acid content of from about 25% to about 50% with a lower alcohol.

9. A process of making the composition according to claim 1, comprising a step of transesterifying a sucrose molecule with a hydrogenated oil that comprises a trans fatty acid content of from about 25% to about 50%.

10. A process according to claim 9, wherein the oil comprises an edible oil.

11. A process according to claim 9, wherein the oil comprises an oil selected from a group consisting of rapeseed oil, tallow oil, coconut oil, babassu oil, corn oil, lard, olive oil, peanut oil, sesame oil, soybean oil, canola oil, palm oil, sunflower oil, safflower oil, cottonseed oil, and combinations thereof.

12. A process of making the composition according to claim 1, comprising the steps of:
   a. partially hydrogenating an oil or methyl ester derived from an oil to produce an oil or methyl ester comprising carbon chains having a trans fatty acid content of from about 25% to about 50%; and
   b. transesterifying a sucrose molecule with the oil or methyl ester comprising carbon chains having a trans fatty acid content of from about 25% to about 50% to produce an esterified sucrose molecule comprising carbon chains having a trans fatty acid content of from about 25% to about 50%.

13. A food product comprising the composition of claim 1 and at least one food ingredient.

14. A food product according to claim 13, wherein the food product comprises, based on total weight of the food product, from about 1% to 99% of the sucrose polyester blend.

15. A food product according to claim 13, wherein the at least one food ingredient is selected from a group consisting of cocoa powder, cocoa butter, chocolate liquor, sugar, non-calorie sweetener, partially or wholly non-digestible carbohydrate bulking agent, triglycerides, emulsifiers, water, fresh egg, sugar, flour, non-pre-gelatinized starch, egg solids, protein solids, flavorings, colorants, and mixtures thereof.

16. A food product according to claim 13, wherein the food product is chocolate.

17. A method of providing a reduced fat content food product having an improved mouth feel comprising a step of incorporating the composition of claim 1 into a food product.

18. A method according to claim 17, wherein the food product is chocolate.

\* \* \* \* \*